(12) United States Patent
Harvie

(10) Patent No.: US 11,446,131 B2
(45) Date of Patent: Sep. 20, 2022

(54) SOFT PROSTHETIC IMPLANT COMPRISING MACRO-TEXTURISATION AND METHOD OF MANUFACTURING

(71) Applicant: GC Aesthetics (Distribution) Limited, Dublin (IE)

(72) Inventor: Fraser Harvie, Glasgow (GB)

(73) Assignee: GC Aesthetics (Distribution) Limited, Dublin (IE)

( * ) Notice: Subject to any disclaimer, the term of this patent is extended or adjusted under 35 U.S.C. 154(b) by 0 days.

(21) Appl. No.: 16/604,136

(22) PCT Filed: Mar. 22, 2018

(86) PCT No.: PCT/EP2018/057285
§ 371 (c)(1),
(2) Date: Oct. 9, 2019

(87) PCT Pub. No.: WO2018/188930
PCT Pub. Date: Oct. 18, 2018

(65) Prior Publication Data
US 2020/0146801 A1    May 14, 2020

(30) Foreign Application Priority Data
Apr. 10, 2017   (GB) ...................................... 1705707

(51) Int. Cl.
*A61F 2/12*    (2006.01)
*A61F 2/00*    (2006.01)

(52) U.S. Cl.
CPC .............. *A61F 2/0077* (2013.01); *A61F 2/12* (2013.01); *A61F 2002/0081* (2013.01);
(Continued)

(58) Field of Classification Search
CPC .................................... A61F 2/12; A61F 2/00
(Continued)

(56) References Cited

U.S. PATENT DOCUMENTS 3,356,090 A * 12/1967 Plantinga .............. A61F 13/141
604/368
3,755,042 A    8/1973 Robertson et al.
(Continued)

FOREIGN PATENT DOCUMENTS

BR    1320 1201 6489 E2    10/2015
CO         7350629          8/2015
(Continued)

OTHER PUBLICATIONS

International Search Report and Written Opinion for Application No. PCT/EP2018/057285, dated Oct. 18, 2018, 15 pages.
(Continued)

*Primary Examiner* — Suzette J Gherbi
(74) *Attorney, Agent, or Firm* — Knobbe, Martens, Olson & Bear, LLP

(57)    ABSTRACT

An implant comprising an implant body, wherein the implant body comprises one or more regions of macro-texturisation on a surface of the implant body. Various methods of making an implant comprising one or more regions of macro-texturisation on a surface of the implant body are described, the methods being (i) making an implant comprising forming a shell on a mandrel, wherein the mandrel is shaped to form regions of macro-texturisation in the shell and filling the shell with a core material; (ii) making an implant comprising securing a scaffold comprising a silicone polymer to a surface of an implant body or (iii) making an implant comprising extruding a material that will form regions of macro-texturisation onto an implant body or (iv) making an implant comprising laser etching a surface on an implant body to form regions of macro-texturisation.

19 Claims, 5 Drawing Sheets

(52) U.S. Cl.
CPC ............. *A61F 2210/0004* (2013.01); *A61F 2230/0065* (2013.01); *A61F 2240/001* (2013.01); *A61F 2250/0031* (2013.01); *A61F 2250/0067* (2013.01); *A61F 2250/0081* (2013.01); *A61F 2250/0096* (2013.01)

(58) Field of Classification Search
USPC .................................................... 623/7–8
See application file for complete search history.

(56) References Cited

U.S. PATENT DOCUMENTS

| | | | |
|---|---|---|---|
| 4,531,244 | A | 7/1985 | Hamas |
| 4,792,336 | A | 12/1988 | Hlavacek et al. |
| 5,500,019 | A | 3/1996 | Johnson et al. |
| 10,765,501 | B2* | 9/2020 | Van Epps ................. A61F 2/12 |
| 10,905,466 | B2 | 2/2021 | Chacon Quiros et al. |
| 11,234,808 | B2 | 2/2022 | Govari et al. |
| 2003/0036803 | A1 | 2/2003 | McGhan |
| 2006/0111777 | A1 | 5/2006 | Chen |
| 2008/0082177 | A1 | 4/2008 | Yang |
| 2009/0012372 | A1 | 1/2009 | Burnett |
| 2009/0125107 | A1 | 5/2009 | Maxwell |
| 2011/0054604 | A1 | 3/2011 | Becker |
| 2011/0082545 | A1 | 4/2011 | Freund |
| 2011/0098576 | A1 | 4/2011 | Hollstien |
| 2011/0106249 | A1 | 5/2011 | Becker |
| 2012/0041555 | A1 | 2/2012 | Manesis |
| 2012/0226352 | A1* | 9/2012 | Becker ................. A61F 2/12 623/8 |
| 2015/0057762 | A1 | 2/2015 | Harms et al. |
| 2015/0112434 | A1 | 4/2015 | Felix et al. |
| 2015/0250582 | A1 | 9/2015 | Greenhalgh et al. |
| 2015/0351900 | A1* | 12/2015 | Glicksman ............ A61B 90/02 623/8 |
| 2015/0359637 | A1* | 12/2015 | Miquel ................... A61F 2/30 623/18.11 |
| 2016/0038269 | A1* | 2/2016 | Altman ................. A61F 2/0063 623/8 |
| 2016/0374720 | A1 | 12/2016 | Anderson et al. |
| 2016/0374797 | A1 | 12/2016 | Nguyen |
| 2017/0049549 | A1* | 2/2017 | Bayat .................. H01J 37/3056 |
| 2018/0092726 | A1* | 4/2018 | Van Epps ................. A61F 2/12 |
| 2018/0110612 | A1* | 4/2018 | Schuessler .............. A61L 27/56 |
| 2019/0125401 | A1 | 5/2019 | Chacon Quiros et al. |
| 2020/0015973 | A1* | 1/2020 | Lindsey ................. A61B 17/68 |
| 2020/0100885 | A1 | 4/2020 | Harvie |
| 2020/0100892 | A1* | 4/2020 | Limem .................... A61F 2/12 |
| 2020/0268499 | A1* | 8/2020 | Hill ............................ A61F 2/12 |
| 2020/0375726 | A1* | 12/2020 | Limem .................... A61F 2/12 |
| 2021/0038367 | A1 | 2/2021 | Harvie |
| 2021/0085443 | A1 | 3/2021 | Kocak et al. |
| 2021/0204976 | A1 | 7/2021 | Chacon Quiros et al. |
| 2022/0054254 | A1 | 2/2022 | Gryskiewicz et al. |

FOREIGN PATENT DOCUMENTS

| | | |
|---|---|---|
| EP | 0 370 292 A1 | 5/1990 |
| EP | 1852040 A1 | 11/2007 |
| EP | 2921137 | 9/2015 |
| EP | 3298962 A1 | 3/2018 |
| WO | WO 2008/055229 A2 | 5/2008 |
| WO | WO 2009/039373 A1 | 3/2009 |
| WO | WO 2012/103611 A1 | 8/2012 |
| WO | WO 2012/177587 A1 | 12/2012 |
| WO | WO 2013/122568 A1 | 8/2013 |
| WO | WO 2015/176014 | 11/2015 |

OTHER PUBLICATIONS

GB Search Report regarding Application No. GB1703631.0, dated Jul. 7, 2017, 3 pages.
"Estudio de copolímeros poli(pdioxanona) / poliglicólico"—2007 (D2 cited in Colombia).

* cited by examiner

SOFT PROSTHETIC IMPLANT COMPRISING MACRO-TEXTURISATION AND METHOD OF MANUFACTURING

CROSS-REFERENCE TO RELATED APPLICATIONS

This application is a U.S. national stage application of International Patent Application No. PCT/EP2018/057285, filed Mar. 22, 2018, which claims the benefit of G.B. Application No. 1705707.6, filed Apr. 10, 2017, the disclosure of each of which is hereby incorporated by reference in its entirety.

The invention relates to implants and methods of making these. In particular, the invention relates to implants comprising macro-texturisation.

Implantable prostheses, in particular soft prosthetic implants, are used to replace or augment body tissue. The most common example of this is breast augmentation or reconstruction, however such implants are also used to modify the appearance of soft tissue in, for instance, the buttocks, chin, calf, abdomen or arms.

Many implants have a textured surface, to reduce capsular contraction and aid retention of the implant in position during post-surgical healing. However, there is a possible link between the use of implants where the implant body has a textured surface, and ALCL (anaplastic large cell lymphoma). In view of this, it could be beneficial to offer implants of alternative design.

Silimed and Polytech Health and Aesthetics each market silicone breast implants under the trade marks BioDesign™ and Microthane™ respectively. These implants are entirely encapsulated in a polyurethane foam with the intention of providing products with reduced capsular contracture.

The invention is intended to overcome or ameliorate at least some aspects of these problems.

Accordingly, in a first aspect of the invention there is provided an implant comprising an implant body. It will generally be the case that the implant body comprises one or more regions of macro-texturisation on a surface of the implant body. The regions of macro-texturisation remove the need for complete surface texturisation (micro-texturisation), whilst addressing both the issue of capsular contraction and ALCL. Capsular contraction is reduced or eliminated by the provision of macro-texturisation, which acts to encourage new soft-tissue growth and prevent implant rotation, flipping or migration. The perceived cause of ALCL is micro-texturisation on the surface of the implant body, this is either entirely absent in the implants of the invention, or the percentage of the total implant surface (surface of the implant body and regions of macro-texturisation combined) including micro-texturisation is significantly reduced. In addition, the absence of total surface micro-texturisation offered by the implants of the invention allows them to be removed more easily and with less damage to the tissue cavity. This is because adhesion is localised.

As used herein, the term "macro-texturisation" is intended to include regions applied to or integrally moulded to the implant body which visibly modify the conventional shape of the implant body, for instance the "round" or "contoured" shapes conventional for breast implants. Such modification is generally clearly visible to the naked eye, and of cross-section in the range 0.1-10 cm. The depth of the region of macro-texturisation could be in the range 0.1-1.5 cm, often 0.15-1.2 cm, 0.2-0.6 cm or 0.3-0.4 cm. In other words, the macro-texturisation could be regarded as a three-dimensional distortion in the surface of the implant body, such as a bump, groove, additional layer or undulation. As such, macro-texturisation is not intended to include, for instance, the texture provided by salting a breast implant, which whilst visible without the use of magnification (for instance from under a microscope), must be viewed with the assistance of a magnifier to be discernable on the level of the pores and undulations created.

For the avoidance of doubt, reference to the "region of macro-texturisation" is intended to include reference to more than one region of macro-texturisation, as a single or multiple regions of macro-texturisation may be present dependent upon the design of the implant.

Often, the implant body is smooth and/or includes regions of micro-texturisation. As used herein, the term micro-texturisation is intended to mean texturisation which may be evident without the use of magnification, but which cannot be seen in detail with the naked eye. Micro-texturisation would generally be of individual cross-section and/or depth in the range 1-100 µm, 5-50 µm or 10-25 µm. Micro-texturisation will most commonly be provided by "salting" the surface of the implant body during manufacture, however, other methods, such as sugaring enveloping the implant body in fabric and then removing (imprinting) may also be used.

The surface of the region of macro-texturisation may be smooth, or include micro-texturisation, for instance from a scaffold material. It will often be the case that the surface of the region of macro-texturisation will have a structure which is different from the surface of the implant body, such that when one includes micro-texturisation, the other doesn't. For instance, the region of macro-texturisation may include micro-texturisation such as from salting, or from a scaffold and the surface of the implant body may be smooth. Alternatively, both may include micro-texturisation but of different types, in such cases, it will most commonly be the case that the surface of the implant body is salted, and the region of macro-texturisation includes a micro-textured scaffold.

It will often be the case that the region of macro-texturisation provides a fixation surface on the implant. As used herein, the term "fixation surface" is intended to refer to a surface which is structured to encourage enhanced adhesion of the implant to the surrounding tissue. As such, the fixation surfaces may be positioned such that after adhesion the implant moves naturally with the body.

The macro-texturisation may be provided by a scaffold secured to a surface of the implant body; or formed by laser etching. Alternatively, the regions of macro-texturisation may be integral to the surface of the implant body. As used herein, the term "scaffold" is intended to mean any substrate, smooth or micro-textured, which is fixed to the surface of the implant body.

It may be that the regions of macro-texturisation are of a configuration selected from a ring configuration comprising a single ring or multiple concentric rings; dots present in a ring; a randomised configuration comprising multiple regions of macro-texturisation, a banded configuration or combinations thereof. It will often be the case that the implant body has a smooth surface, and that any texturisation is provided by the regions of macro-texturisation. Micro-texturisation may be present on the surface of the regions of macro-texturisation as this can help promote tissue adhesion, but it is not essential. Alternatively the scaffold may be a web-like structure formed directly on the surface of the implant. The web will generally be formed from a material that is fluid prior to curing or drying, such that the web can be formed by extrusion of the scaffold web onto the surface of the implant. As a result, the web will typically comprise a polymeric material, such as those described below. Often, the web will comprise the material used to form the surface of the implant body, to provide maximum adhesion of the web to the implant body after curing/drying of the web.

The implant may be a breast implant, and in such cases the regions of macro-texturisation may be of a banded configuration comprising one or more bands positioned at the point of the implant which will rest in the infra-mammary fold. This can be particularly beneficial in contoured (anatomical) breast implants as the asymmetric nature of the implant body makes it particularly important that flipping, rotation and migration away from the original positioning be achieved. This can be done particularly effectively by controlling positioning at the infra-mammary fold. Often in this configuration the regions of macro-texturisation will be formed from a scaffold.

Alternatively, where the implant is a breast implant, in particular a round breast implant, the regions of macro-texturisation may be around the circumference of the implant, either as a band extending around the circumference of the implant or as a series of dots around the circumference. In the band configuration, the region of macro-texturisation will often be formed from a scaffold, in the dot configuration the regions of macro-texturisation may be integral or formed from a scaffold. In the band configurations, it will often be the case that the implant body will have a smooth surface, however, it may be that the implant body has a micro-textured surface which is obscured by regions of macro-texturisation on the front and back of the implant, those regions of macro-texturisation having smooth surfaces such that the overall properties of the implant are similar to the configuration where a band or series of dots is provided around the circumference.

Where the implant is a breast implant, it may be that the ring configurations described above, namely single or multiple concentric rings, are present. It will often be the case, where the ring configuration is adopted, that the rings will be on the back of the implant as it is placed in the tissue cavity. This promotes location and tissue adhesion. Alternatively, for instance if the surface of the implant body includes micro-texturisation, the regions of macro-texturisation may be smooth and may be present on the front of the breast implant, such that a micro-textured rear surface is provided for tissue adhesion. The ring configurations would be used most frequently with round breast implants, and may be present as a scaffold or integrally moulded region of macro-texturisation. The scaffold may be surface extruded macro-texturisation.

Additionally or alternatively to providing fixation surfaces, the regions of macro-texturisation may function as implant orientation markers. An implant orientation marker provides a positional indicator to the surgeon, assisting in the correct alignment of the implant in the body cavity. As the orientation markers are often co-incident with the regions where early ingrowth of soft tissue is important, it can be advantageous if the regions of macro-texturisation offer both fixation surfaces and orientation markers.

The implant will typically be a soft prosthetic implant, often for augmentation or reconstruction of the buttocks, breast, chest, calf, abdomen or arm. As such, the implant will often be an implant selected from buttock, breast, chest, calf, abdominal and arm implants. In many cases, the implant is a breast implant. Where the implant is a breast implant this may be a round or contoured (anatomical teardrop).

The regions of macro-texturisation and/or the implant body may comprise a bioactive material. This can help to reduce in particular microbial contamination of the implant prior to surgery, reduce/eliminate microbial growth during healing and at later stages post implantation and promote tissue adhesion and in growth. In many cases, it may be that the regions of macro-texturisation and/or the implant body are coated and/or impregnated with a bioactive material. This can reduce costs as the bioactive is present only at the surface of the implant, namely the region of the implant where the bioactive material is of most use. The bioactive material may comprise an antibiotic, antimicrobial, biocide, anti-inflammatory drug, steroid, isolated adipose cells, or combinations thereof. Adipose cells may be present if, in addition to the shaping provided by the implant, fat reconstruction is also desired. This will most commonly be where the implant surgery is for reconstructive purposes.

One or more of the regions of macro-texturisation and/or the implant body may comprise any polymer commonly used as an implant material, in particular the polymer may be a synthetic polymer (resorbable or non-resorbable), or combination of synthetic polymers.

One or more of the regions of macro-texturisation and/or the implant body may comprise a silicone polymer. Silicone polymers are non-resorbable and are desirable as they are biocompatible. Further, silicone polymers have been used for many years in the implant field, resulting in high consumer confidence in this material. Additionally, silicone polymers can be formed to mimic soft tissue. It may be that the silicone polymer is selected from polydimethylsiloxane, polysiloxane, polyfluorosiloxane and/or phenylsiloxane combinations thereof.

It may be that one or more of the regions of macro-texturisation and/or implant body comprise a further non-resorbable polymer selected from polyurethane, polyester, polypropylene, polycarbonate, polyethylene, polybutylene, polymethyl methacrylate, polyvinyl chloride, polytetrafluoroethylene, polyethylene glycol, polyethylene oxide or combinations thereof. Polyurethane is used less often than the other polymers described above as it is believed to degrade in situ to toluene diisocyanate and 2,4 toluene diamine, both of which may be carcinogenic. Further, it has been shown that where the polyurethane is present as a foam coating, capsular contracture can occur.

It may be the case that one or more of the regions of macro-texturisation is at least partially resorbable, in which case the region of macro-texturisation will typically be a scaffold. This can be desirable as the scaffold provides initial prevention of rotation or flipping of the implant in the tissue cavity, but will slowly resorb via hydrolysis as new soft tissue grows into the scaffold and around the implant. This erosion (resorbtion) provides support for the soft tissue as it forms around the implant, whilst at the same time ensuring that the soft tissue can grow to the surface of the implant body during post-surgical healing, providing the implant with full support. As such, the scaffold may comprise a polymer selected from polylactic acid, polyglycolic acid, polycaprolactone, polytrimethylene carbonate, polyhydroxybuterate, polyhydroxyoxyvalerate, combinations thereof or combinations of these polymers with a silicone polymer or the other non-resorbable polymers described above.

Often, where the region of macro-texturisation is a scaffold, this may be any three-dimensional interconnected architecture, such as a foam, a felt, a non-woven material, a knitted material, a mesh, a woven textile, a 3D printed material, a fibre-spun material, a laminate or combinations thereof in 2D or 3D. Such structures encourage soft-tissue ingrowth thereby preventing rotation, flipping or migration of the implant. It will often be the case that the scaffold comprises a foam, as foams (in particular polysiloxane foams), have similar properties to soft tissue, resulting in enhanced compatibility with the cavity tissue. Further, the porous nature of the foam allows it to act as a reservoir for any active ingredients, such as the bio-actives described above, that may be impregnated in the regions of macro-texturisation and/or implant body.

It may be the case that the scaffold is porous, the porosity being provided by a foam or other scaffold construction. The presence of pores (symmetrical or asymmetrical) allows for easy impregnation with bio-actives and also for the ingress of soft tissue during post-surgical healing. Where the scaffold is porous, it may be that it comprises pores of mean diameter in the range 10-1000 µm, often 80-550 µm, often 200-475 µm. As used herein, the term "diameter" is intended to mean the measurement across the largest cross-section of the pore. Often the scaffold will have a pore density in the range 25-150 pores per inch, often 80-120 or roughly 100 pores per inch. Where present, the pores will have a connectivity, often this will be in the range 85-99.9%. This connectivity is significantly higher than is provided by most commercial grade foams, ensuring that tissue growth is encouraged from all directions where the scaffold is present. It is calculated that the inter-connection pore diameters in the porous systems described above would be in the range 75-200 µm, often having a mean inter-connection pore diameter in the range 100-200 µm, or around 150 µm. A porous structure with one or more of the porous properties described above (mean pore diameter, pore density, connectivity) will have characteristics that closely mimic soft tissue, providing a natural feel, comparable mechanical properties, good biocompatibility and comfort. The more of the properties present the closer the mimic the foam scaffold provides.

It may be the case that laser etching is used to form the macro-texturisation or micro-texturisation. Laser etching has benefits similar to the use of an extruded scaffold, in that the macro-texturisation is formed from the same material as the surface of the implant body, ensuring good compatibility, and the degree of control in the formation of the macro-texturisation is very high. Where laser etching is used the depth of the macro-texturisation is measured by the depth of material cut-away in the etching process.

In a second aspect of the invention, there is provided a method of making an implant comprising forming a shell on a mandrel, wherein the mandrel is shaped to form regions of macro-texturisation in the shell, and filling the shell with a core material. Typically, the core material will then be cured. This method provides a rapid and simple method of forming integral regions of macro-texturisation on the implant surface, without requiring significant changes in conventional production systems.

In a third aspect of the invention, there is provided an alternative method of making an implant, the method comprising securing a scaffold to a surface of an implant body, it will generally be the case that the scaffold comprises a silicone polymer, a resorbable polymer or combination thereof, often in the form of a foam.

It may be that securing of the scaffold to the implant body comprises one or more steps selected from: application of the scaffold to an outer layer of an unvulcanised implant body with subsequent vulcanisation; applying an unvulcanised layer of implant body material to the scaffold, applying the scaffold to an outer layer of a vulcanised implant body and vulcanising the unvulcanised material; gluing the scaffold to the implant body. These methods provide secure, biocompatible, adherence of the scaffold to the implant body. Where gluing is used, it may be that gluing comprises using a glue selected from room temperature vulcanising silicone glue, UV cure isocyanate glue and/or moisture cure isocyanate glue.

In a fourth aspect of the invention there is provided a yet further method of making an implant, the method comprising extruding a material that will form regions of macro-texturisation onto an implant body. This method has the advantage of providing excellent control over the shape of the region of macro-texturisation, and is particularly suitable for forming web-structures. Where the method comprises extruding a material onto an implant body, it will often be the case that the method further comprises curing or drying of the material. This allows for the use of a wider range of synthetic polymers, and in particular for the use of silicone polymers which are favoured because of their biocompatibility.

In a fifth aspect of the invention there is therefore provided a yet further method of making an implant, the method comprising laser etching a surface of an implant body to form regions of macro-texturisation. Laser etching may be used in combination with the method of making an implant comprising forming a shell on a mandrel, wherein the mandrel is shaped to form regions of macro-texturisation in the shell, and filling the shell with a core material. This method has the advantage of providing excellent control over the shape of the region of macro-texturisation.

In a sixth aspect of the invention there is provided a method of tissue augmentation or reconstruction comprising surgically inserting an implant of the first aspect of the invention into the tissue cavity of a human or animal. Typically the surgery will be on a human. Typically the surgery will be buttock, breast, chest, calf or abdominal augmentation or reconstruction, and most often breast augmentation or reconstruction.

There is therefore provided, an implant comprising an implant body, wherein the implant body comprises one or more regions of macro-texturisation (cross-section in the range 0.1 cm-10 cm, depth in the range 0.1 cm-1.5 cm) on a surface of the implant body. The implant body may be smooth and/or include regions of micro-texturisation. The region of macro-texturisation may provide a fixation surface and/or an orientation marker on the implant. The macro-texturisation is optionally provided by a scaffold secured to a surface of the implant body, the scaffold may comprise a web formed directly on the surface of the implant, or often a foam. Alternatively, the regions of macro-texturisation are integral to the surface of the implant body. The regions of macro-texturisation and/or the implant body may comprise a bioactive material, a resorbable polymer or a non-resorbable polymer, such as a silicone polymer.

There are also provided a number of methods for making an implant, including:

forming a shell on a mandrel, wherein the mandrel is shaped to form regions of macro-texturisation in the shell and filling the shell with a core material and curing the core material;

securing a scaffold comprising a silicone polymer to a surface of an implant body wherein securing of the scaffold to the implant body comprises one or more steps selected from: application of the scaffold to an outer layer of an unvulcanised implant body with subsequent vulcanisation; applying an unvulcanised layer of implant body material to the scaffold, applying the scaffold to an outer layer of a vulcanised implant body and vulcanising the unvulcanised material; gluing the scaffold to the implant body;

extruding a material that will form regions of macro-texturisation onto an implant body and drying or curing the material; and laser etching a surface of an implant body to form regions of macro-texturisation.

Unless otherwise stated each of the integers described may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

In order that the invention may be more readily understood, it will be described further with reference to the figures and to the specific examples hereinafter.

FIG. 6a shows a light surface coverage of macro-texturisation, and FIG. 6b shows a high degree of surface coverage of macro-texturisation;

FIG. 7a shows light micro-texturisation and FIG. 7b shows heavier micro-texturisation.

Figure 1:
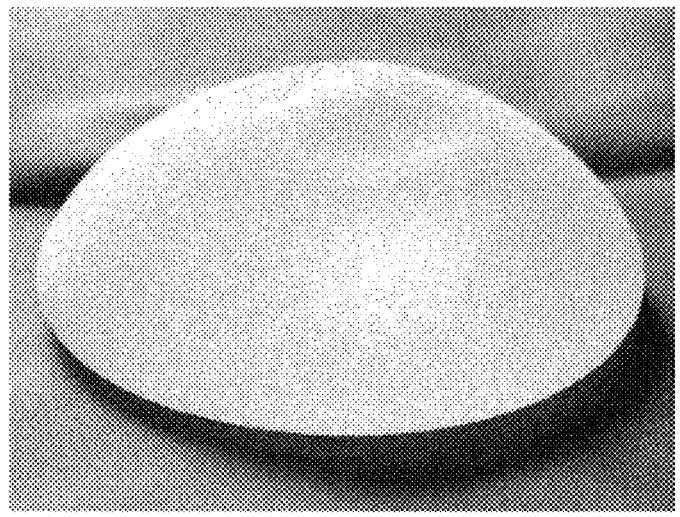
FIG. 1 is an image of a prior art implant including salted surface micro-texturisation.
Figure 2:
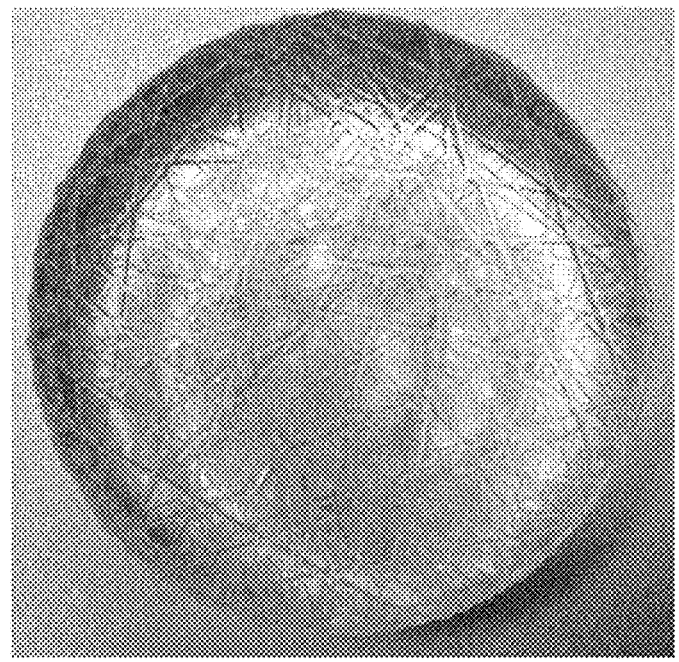
FIG. 2 is an image of a breast implant comprising a smooth implant body and an extruded scaffold of macro-texturisation.
Figure 3:
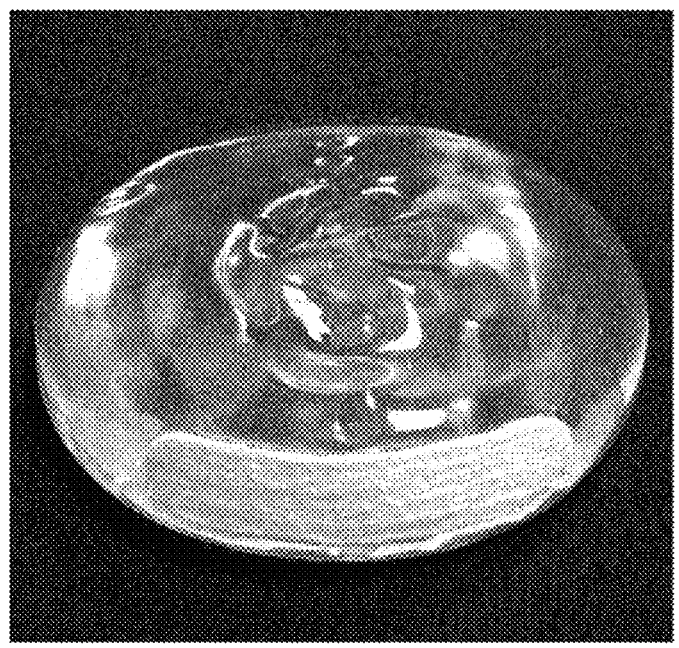
FIG. 3 is an image of a breast implant comprising a smooth implant body and a fabric scaffold fixation surface and orientation marker identifying the part of the implant which should be positioned at the infra-mammary fold.
Figure 4:
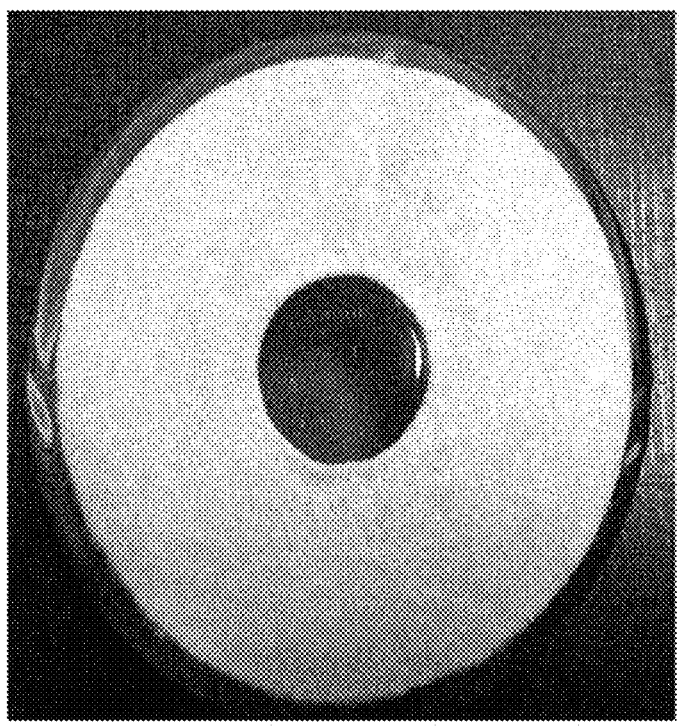
FIG. 4 is an image of a breast implant comprising a smooth implant body and a felted fabric scaffold on a rear surface of the implant.
Figure 5:
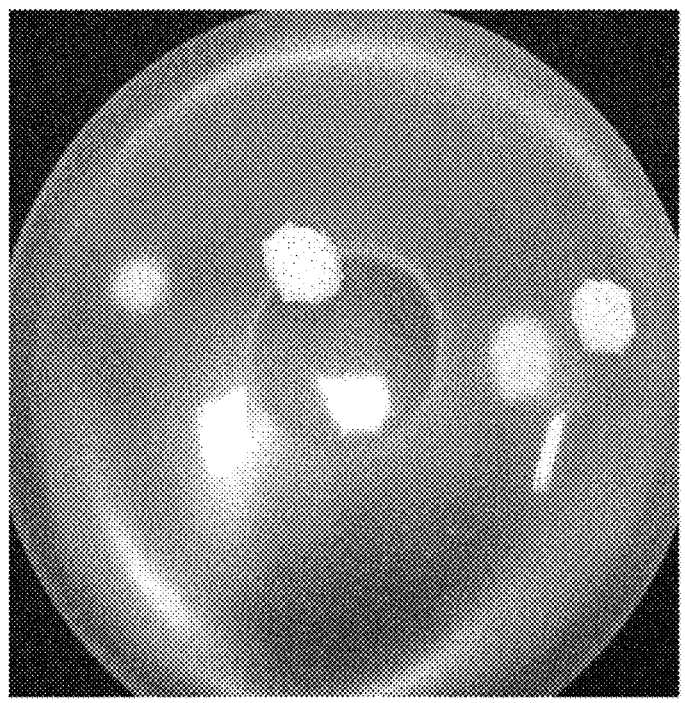
FIG. 5 is an image of a breast implant comprising a smooth implant body and randomised dots of silicone foam scaffold macro-texturisation.
Figure 6A:
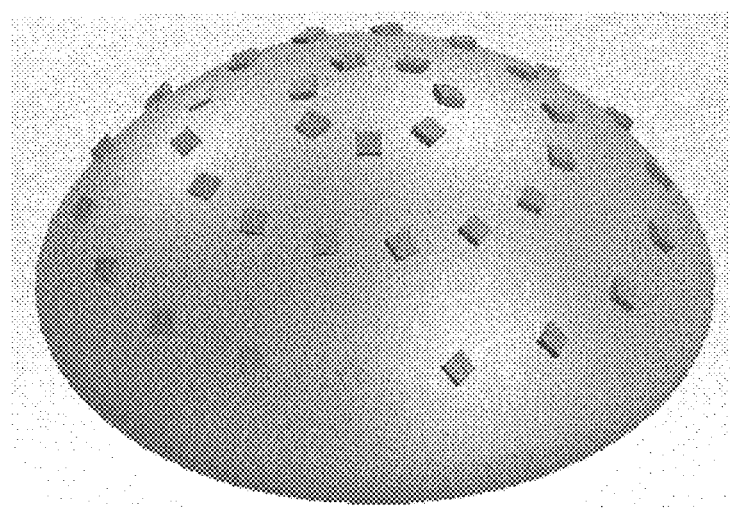
FIGS. 6a and 6b are schematic images of a breast implant comprising integral macro-texturisation as though prepared using a texturised mandrel.
Figure 6B:
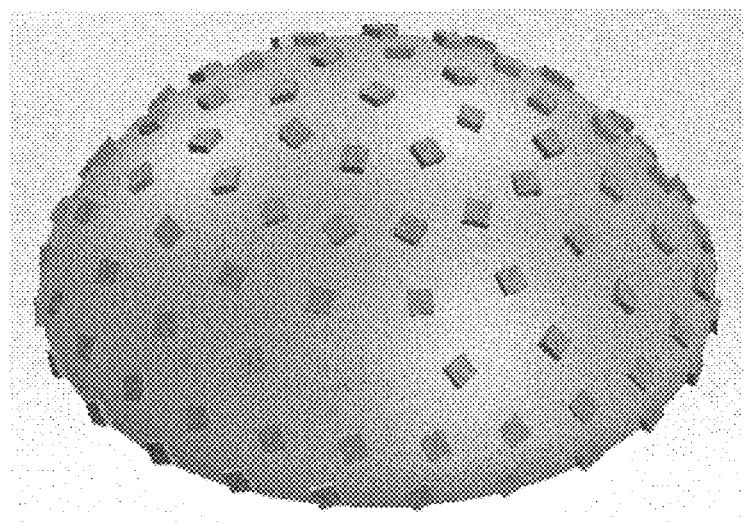
Figure 7A:
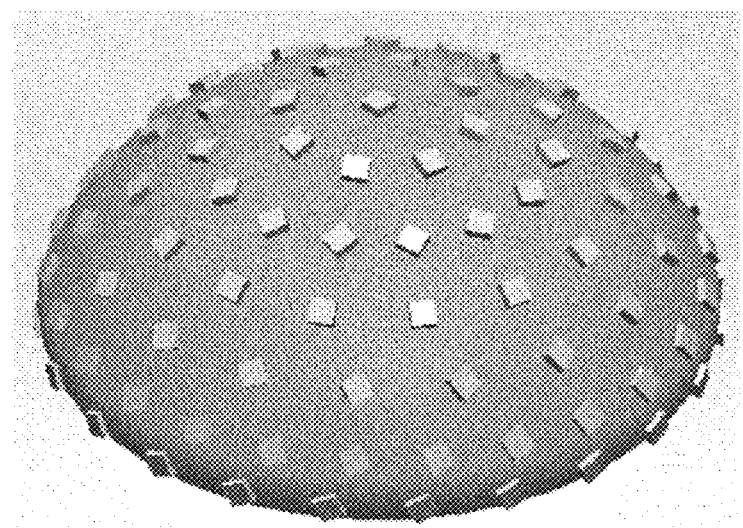
FIGS. 7a and 7b are schematic images of a breast implant comprising a micro-texturised body and a smooth scaffold.
Figure 7B:
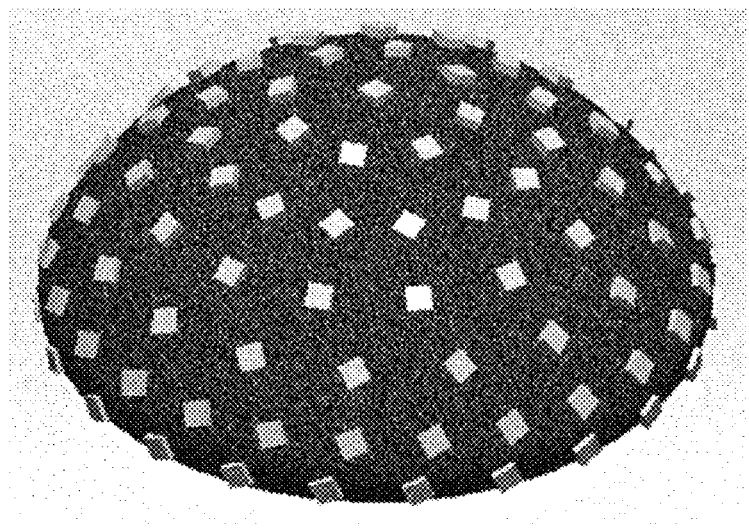
Figure 8:
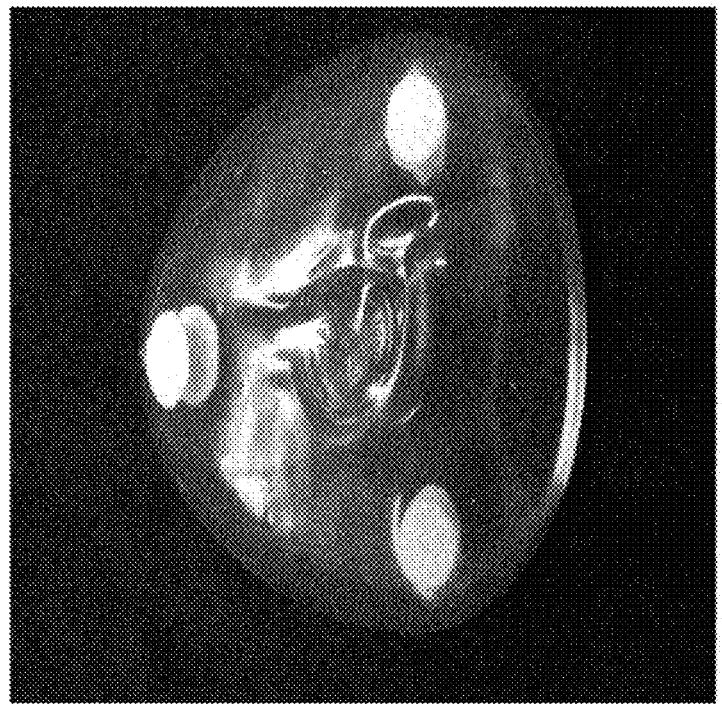
FIG. 8 is an image of a gluteal implant comprising a smooth implant body and felted dots of macro-texturisation.

FIG. 1 shows a typical micro-texturised round salted breast implant. FIGS. 2-6 and 8 show implants of the invention. In these examples the surface of the implant body is smooth, with regions of macro-texturisation being provided to assist tissue ingrowth, and positioning. FIG. 2 shows an implant made using extrusion techniques, where the polymeric web is formed directly on the surface of the implant. FIG. 7 shows an implant of the invention with a salted surface of the implant body, and smooth regions of macro-texturisation.

With the exception of surface modification, manufacture is using conventional techniques. Surface modification may be integral, using formation on a modified mandrel, as in FIG. 6, or through the provision of a scaffold, as in FIGS. 2-6 and 8 or via laser etching.

It should be appreciated that the implants and methods of the invention are capable of being implemented in a variety of ways, only a few of which have been illustrated and described above.

The invention claimed is:

1. A soft prosthetic implant for augmentation or reconstruction comprising an implant body, wherein the implant body comprises one or more regions of macro-texturisation on a surface of the implant body, wherein the macro-texturisation is provided by a scaffold secured to a surface of the implant body, wherein the scaffold is at least partially resorbable, and wherein the one or more regions of macro-texturisation is of cross-section in the range 0.1 cm-10 cm and/or of depth in the range 0.1 cm-1.5cm.

2. An implant according to claim 1, wherein the implant body is smooth and/or includes regions of micro-texturisation.

3. An implant according to claim 1, wherein the one or more regions of macro-texturisation provide a fixation surface on the implant body.

4. An implant according to claim 1, wherein the scaffold comprises a web formed directly on the surface of the implant body.

5. An implant according to claim 1, wherein the one or more regions of macro-texturisation are of a configuration selected from a ring configuration comprising a single ring or multiple concentric rings, a randomised configuration comprising multiple regions of macro-texturisation, a banded configuration or combinations thereof.

6. An implant according to claim 1, wherein the implant is a breast implant and the one or more regions of macro-texturisation are of a banded configuration comprising one or more bands positioned at the point of the implant which will rest in the infra-mammary fold.

7. An implant according to claim 1, wherein the one or more regions of macro-texturisation function as implant orientation markers.

8. An implant according to claim 1, wherein the one or more regions of macro-texturisation and/or the implant body comprise a bioactive material.

9. An implant according to claim 8, wherein the one or more regions of macro-texturisation and/or the implant body are coated and/or impregnated with a bioactive material.

10. An implant according to claim 1, wherein the scaffold comprises a foam, a felt, a non-woven material, a knitted material, a mesh, a woven textile, a 3D printed material, a fibre-spun material, a laminate or combinations thereof.

11. A method of making a soft prosthetic implant comprising forming one or more regions of macro-texturisation on an implant body by securing an at least partially resorbable scaffold to a surface of the implant body, wherein securing of the scaffold to the implant body comprises one or more steps selected from: application of the scaffold to an outer layer of an unvulcanised implant body with subsequent vulcanisation; applying an unvulcanised layer of implant body material to the scaffold, applying the scaffold to an outer layer of a vulcanised implant body and vulcanising the unvulcanised material; and gluing the scaffold to the implant body.

12. A method according the claim 11, wherein the scaffold further comprises a silicone polymer.

13. A method according to claim 11, wherein securing the scaffold comprises the gluing, and the comprises using a glue selected from room temperature vulcanising silicone glue, UV cure isocyanate glue and/or moisture cure isocyanate glue.

14. A method according to claim 11, wherein forming the one or more regions of macro-texturisation on the implant body further comprises extruding a material that will form the regions of macro-texturisation onto the implant body.

15. A method of tissue augmentation or reconstruction comprising surgically inserting the implant of claim 1 into a tissue cavity of a human or animal.

16. An implant according to claim 8, wherein the bioactive material comprises an antibiotic, antimicrobial, biocide, anti-inflammatory drug, steroid, isolated adipose cells or combinations thereof.

17. An implant according to claim 1, wherein the scaffold comprises a polymer selected from polylactic acid, polyglycolic acid, polycaprolactone, polytrimethylene carbonate, polyhydroxybuterate, polyhydroxyoxyvalerate and combinations thereof.

18. An implant according to claim 1, wherein the scaffold further comprises a polymer selected from silicone, polyurethane, polyester, polypropylene, polycarbonate, polyethylene, polybutylene, polymethyl methacrylate, polyvinyl chloride, polytetrafluoroethylene, polyethylene glycol, polyethylene oxide and combinations thereof.

19. An implant according to claim 1, wherein the scaffold further comprises a silicone polymer selected from polydimethylsiloxane, polysiloxane, polyfluorosiloxane, phenylsiloxane and combinations thereof.

* * * * *

UNITED STATES PATENT AND TRADEMARK OFFICE
CERTIFICATE OF CORRECTION

PATENT NO. : 11,446,131 B2
APPLICATION NO. : 16/604136
DATED : September 20, 2022
INVENTOR(S) : Fraser Harvie It is certified that error appears in the above-identified patent and that said Letters Patent is hereby corrected as shown below:

In the Specification

On Column 4, Line 50: delete "(resorbtion)" and insert -- (resorption) --.

On Column 4, Line 57: delete "polyhydroxyoxyvalerate," and insert -- polyhydroxyvalerate, --.

In the Claims

On Column 8, Line 64: In Claim 12, delete "the" and insert -- to --.

On Column 8, Line 67: In Claim 13, after "the" insert -- gluing --.

On Column 9, Line 18: In Claim 17, delete "polyhydroxyoxyvalerate" and insert -- polyhydroxyvalerate --.

Signed and Sealed this
Tenth Day of January, 2023

Katherine Kelly Vidal
*Director of the United States Patent and Trademark Office*